US012262944B2

United States Patent
Ortega Quijano et al.

(10) Patent No.: US 12,262,944 B2
(45) Date of Patent: Apr. 1, 2025

(54) DEVICE FOR SAFELY CUTTING BIOLOGICAL TISSUES

(71) Applicant: Deneb Medical, S.L., San Sebastián (ES)

(72) Inventors: Noé Ortega Quijano, San Sebastián (ES); Oliver Rubio Zamora, Irún (ES); Javier Laguardia Arraiza, Pamplona (ES); Juan Arregui Altuna, San Sebastián (ES); Pablo Sacristán González, San Sebastián (ES)

(73) Assignee: Deneb Medical, S.L. (ES)

( * ) Notice: Subject to any disclaimer, the term of this patent is extended or adjusted under 35 U.S.C. 154(b) by 0 days.

(21) Appl. No.: 18/288,150

(22) PCT Filed: May 7, 2021

(86) PCT No.: PCT/ES2021/070319
§ 371 (c)(1),
(2) Date: Oct. 24, 2023

(87) PCT Pub. No.: WO2022/234161
PCT Pub. Date: Nov. 10, 2022

(65) Prior Publication Data
US 2024/0206970 A1    Jun. 27, 2024

(51) Int. Cl.
*A61B 18/20* (2006.01)
*G16H 40/63* (2018.01)
*A61B 17/00* (2006.01)
*A61B 18/00* (2006.01)
*A61B 90/00* (2016.01)

(52) U.S. Cl.
CPC ........... *A61B 18/203* (2013.01); *G16H 40/63* (2018.01); *A61B 2017/00057* (2013.01);
(Continued)

(58) Field of Classification Search
CPC ........ A61B 18/20; A61B 18/203; A61B 90/37; A61B 2090/3735; A61B 2090/376
(Continued)

(56) References Cited

U.S. PATENT DOCUMENTS 4,672,963 A * 6/1987 Barken .................. A61B 18/20
606/12
6,652,512 B2 * 11/2003 Ota ....................... A61B 18/203
606/17
(Continued)

FOREIGN PATENT DOCUMENTS

AU    2016 203 088 B2    2/2017
EP         2480153 B1    8/2016
(Continued)

OTHER PUBLICATIONS

International Search Report for PCT/ES2021/070319 mailed Jan. 24, 2022. 5 pgs.
(Continued)

*Primary Examiner* — Ahmed M Farah
(74) *Attorney, Agent, or Firm* — Lerner David LLP

(57) ABSTRACT

The present invention relates to a device for sectioning biological tissues during a surgical intervention and the use of said device. In particular, the sectioning is safely performed by means of a laser without penalizing the speed of actuation thereof. The device combines information about the laser, information about the tissue, and information about the user in order to apply safety measures.

30 Claims, 5 Drawing Sheets

(52) U.S. Cl.
CPC .............. *A61B 2018/00601* (2013.01); *A61B 2018/00642* (2013.01); *A61B 2018/00708* (2013.01); *A61B 2018/00738* (2013.01); *A61B 2018/00904* (2013.01); *A61B 2090/3735* (2016.02); *A61B 2218/002* (2013.01)

(58) Field of Classification Search
USPC ........................................................ 606/9–12
See application file for complete search history.

(56) References Cited

U.S. PATENT DOCUMENTS

| | | | | |
|---|---|---|---|---|
| 7,108,690 | B1 * | 9/2006 | Lefki | A61B 18/203 606/9 |
| 8,821,482 | B2 * | 9/2014 | Verhagen | A61B 5/442 606/17 |
| 10,265,126 | B2 | 4/2019 | Bruno et al. | |
| 2006/0052661 | A1 * | 3/2006 | Gannot | A61B 1/042 606/11 |
| 2016/0175049 | A1 * | 6/2016 | Chlon | A61B 18/203 606/9 |
| 2017/0011501 | A1 * | 1/2017 | Gonzalez | A61F 9/00825 |
| 2017/0215962 | A1 * | 8/2017 | Aharon | A61B 90/361 |
| 2019/0076195 | A1 | 3/2019 | Shalayev et al. | |
| 2019/0125445 | A1 * | 5/2019 | Garcia | A61N 5/0616 |
| 2024/0225730 | A1 * | 7/2024 | Rubio Zamora | A61B 34/32 |

FOREIGN PATENT DOCUMENTS

| | | |
|---|---|---|
| EP | 3117792 B1 | 7/2019 |
| WO | 2018/136622 A1 | 7/2018 |

OTHER PUBLICATIONS

Zhang, Yaokun et al. "Optical coherence tomography guided laser cochleostomy: towards the accuracy on tens of micrometer scale." BioMed research international vol. 2014 (Sep. 2014): 251814. doi:10.1155/2014/251814. 11 pgs.

Ohmi, Masato, et al, "Real-time OCT imaging of laser ablation of biological tissue," Proc. SPIE 7562, Optical Interactions with Tissues and Cells XXI, 756210 (Feb. 23, 2010); https://doi.org/10.1117/12.840866 <https://doi.org/10.1117/12.840866>. 6 pgs.

Leung, B.Y.C., et al., "Real-time guidance of thermal and ultrashort pulsed laser ablation in hard tissue using inline coherent imaging". Lasers Surg. Med., 44: 249-256 (Jan. 2012), <https://doi.org/10.1002/lsm.21162>. 8 pgs.

Fuchs, Alexander, et al. "Fast and automatic depth control of iterative bone ablation based on optical coherence tomography data", Proc. SPIE 9542, Medical Laser Applications and Laser-Tissue Interactions VII, 95420P (Jul. 15, 2015); <https://doi.org/10.1117/12.2183695>. 6 pgs.

Fuchs, A., et al. "Online measurement and evaluation of the Er:YAG laser ablation process using an integrated OCT system". Biomedizinische Technik. Biomedical engineering. 57. 10.1515/bmt-2012-4231, (Aug. 2012). 4 pgs.

Diaz JD, et al., "Towards intra-operative OCT guidance for automatic head surgery: first experimental results". Med Image Comput Comput Assist Interv. Sep. 2013;16(Pt 3):347-354. doi:10.1007/978-3-642-40760-4_44. 8 pgs.

Boppart, S A et al. "High-resolution optical coherence tomography-guided laser ablation of surgical tissue." The Journal of surgical research vol. 82,2 (Apr. 1999): 275-84. doi:10.1006/jsre.1998.5555. 10 pgs.

* cited by examiner

DEVICE FOR SAFELY CUTTING BIOLOGICAL TISSUES

CROSS-REFERENCE TO RELATED APPLICATIONS

The present application is a national phase entry under 35 U.S.C. § 371 of International Application No. PCT/ES2021/070319, filed May 7, 2021.

Object of the Invention

The present invention relates to a device for sectioning biological tissues during a surgical intervention and the use of said device. In particular, the sectioning is safely performed by means of a laser without penalizing the speed of actuation thereof. The device combines information about the laser, information about the tissue, and information about the user in order to apply safety measures.

BACKGROUND OF THE INVENTION

In surgical applications, laser-based devices present significant advantages with respect to conventional mechanical tools, such as a surgical blade, saw, drill, or a piezoelectric tool. Among said advantages, precision, sectioning with arbitrary geometries, the absence of vibrations, better tissue recovery, and the absence of contact, stand out. However, the absence of contact has the drawback of losing haptic feedback, and thereby losing control over the extent of the sectioning in terms of depth.

With the mechanical instruments conventionally used in surgery, the surgeon does receive this haptic feedback, where the depth of the sectioning to be performed can be controlled at all times. Therefore, the actuation of a mechanical tool is always limited in space, as a result of which said tool only modifies the part it is in contact with physically. In contrast, in laser-based devices, laser propagates in a rectilinear manner and can act on the tissue without any contact and control that limits the sectioning; i.e., the laser does not have an actuation point, but rather an actuation direction. Accordingly, there is an obvious problem in assuring the safety of laser sectioning for surgical applications.

Some solutions to this problem proposed in the state of the art seek to estimate up to where the laser can penetrate based on measurements of the surface of the tissue to be sectioned. In solutions of this type, the process is performed by intercalating the measurements of the surface of the tissue with the sectioning of said tissue in an iterative verification process. This has a significant drawback in terms of the total duration of the sectioning procedure, making these solutions rather unviable in real surgeries.

Additionally, in some of these solutions, tissue sectioning is performed at a single point, the sectioning is caused to progress in said position until reaching the end, and movement to the next sectioning position is only carried out when the preceding one has been completed. This has the drawback that the measurement of the surface of the tissue may become extremely difficult in deep and narrow individual holes or in the presence of irregular or angular shapes on the surface.

Moreover, these solutions present another series of drawbacks that do not assure safety in tissue sectioning because either they do not define the initial region in which one or more tissues will be sectioned well or they do not define the end of a tissue to be sectioned at all, or they do so with little precision or only for tissues having specific characteristics (for example, hard tissues), requiring in this case additional image processing techniques or limiting the application of the solutions to very specific surgeries. These limitations in the definition of the safety mechanisms for tissue sectioning may lead to an unsuitable sectioning, and accordingly an unsatisfactory surgery.

DESCRIPTION OF THE INVENTION

The present invention proposes a solution to the preceding problems by means of a biological tissue sectioning device and the use of the device. The dependent claims define the preferred embodiments of the invention.

A first inventive aspect provides a biological tissue sectioning device, comprising:
  a laser emitter adapted for sectioning biological tissue in a region;
  a controller, in communication with the laser emitter, adapted for activating and deactivating the laser emitter;
  an optical module adapted for determining the surface of a tissue of the region in the operating mode;
  a central processing unit, in communication with the controller and with the optical module, adapted for:
    defining a pre-established sectioning depth of the laser emitter;
    defining at least one reference surface;
    generating a numerical model of the region comprising, at least:
      the shape of the surface of the tissue of the region,
      the shape of the at least one reference surface, under which sectioning is prohibited,
      the direction of the laser beam in which the laser emitter is oriented;
    activating the laser emitter if, in the numerical model, the position corresponding to a point of the straight line, representing the laser beam, and spaced from the intersection of the same straight line with the surface of the tissue by a distance equal to the sectioning depth, is located outside a prohibited region, said prohibited region being any of the parts of the tissue of the region in which sectioning is prohibited.

This first inventive aspect defines a biological tissue sectioning device capable of assuring safety during sectioning without comprising the speed of the procedure. In one example, the device according to the invention sections a volume of biological bone tissue measuring 10×10×10 cubic millimeters in a range of between 50 and 400 seconds.

This sectioning device comprises a laser emitter, i.e., a laser beam or simply laser, in communication with a controller which activates or deactivates it. Preferably, this laser emitter is of the Er:YAG type with a typical emission wavelength of 2940 nanometers. To assure safety during sectioning, the surface of the tissue to be sectioned must be known, for which the sectioning device further comprises an optical module. Said optical module is based on optical topological techniques comprising, for example, an optical coherence tomography system, or structured light, or stereo pair; or on hybrid technologies comprising, for example, an optoacoustic tomography system. Additionally, the optical module comprises computational means capable of identifying the shape of the surface of the tissue based on the measurements taken by the optical or optoacoustic systems.

Moreover, the sectioning device comprises a central processing unit in communication with the controller and with the optical module. Throughout the document, central processing unit will be understood to mean a unit which is capable of receiving and transmitting data, as well as processing said data. In a preferred example, the central processing unit is a processor or a microprocessor.

On one hand, this central processing unit defines a pre-established sectioning depth of the laser emitter, with sectioning depth being understood to mean the depth at which the laser can perform sectioning, measured from the position of the intersection of the straight line defining the laser with the biological tissue. Preferably, the sectioning depth of the laser emitter ranges between 50 micrometers and 200 micrometers.

On the other hand, the central processing unit defines at least one reference surface under which sectioning is not allowed. Said reference surface or surfaces are defined taking into consideration different criteria, such as the demarcation of the end of a tissue, the demarcation of the start of a tissue, a pre-established maximum depth, or a pre-established maximum flat level. Furthermore, said reference surfaces are dynamic, that is, new reference surfaces can be added, pre-existing ones can be modified and/or eliminated, throughout the surgical intervention.

The shape of these reference surfaces, as well as the shape of the surface of the tissue determined by the optical module, are imported to the numerical model generated by the central processing unit. Surfaces corresponding to physical entities acquired by means of measurement devices, such as the surface of the tissue, or virtual surfaces, such as reference surfaces that can be defined, for example, by a user, can be represented in said numerical model. Additionally, said numerical model comprises the direction of the laser beam in which the laser is oriented. The numerical model allows determining intersections and/or conditions based on which decisions can be made. In a preferred example, the numerical model is computationally depicted by means of a data structure which at least allows defining a domain and the geometric entities related to surfaces and actuation lines of the laser.

This numerical model allows determining whether or not the laser must be activated depending on whether safety criteria based on the defined reference surface or surfaces are met. As a result of the numerical model, the position of a point of the straight line, representing the laser beam, spaced from the intersection of the same straight line with the surface of the tissue by a distance equal to the sectioning depth, is determined. The central processing unit then evaluates if said position is located in a prohibited region, with prohibited region being understood to mean any of the parts of the tissue of the region in which sectioning is prohibited. In particular, a prohibited region is the tissue region existing below one of the reference surfaces.

The laser is thereby prevented from sectioning the tissues or parts of tissues of the region which are not the object of the surgery. These safety measures are essential, especially when the non-target tissues are particularly critical, such as nerves, dura mater, or blood vessels.

It should be pointed out that, if there is more than one reference surface, these surfaces must be considered jointly; i.e., the activation and deactivation of the laser will depend on all of these surfaces simultaneously. Therefore, when one of the reference surfaces fails to meet the laser activation criterion, the central processing unit will not activate the laser even though the rest of the reference surfaces meet said activation criterion.

Therefore, by means of the device of the first inventive aspect, the central processing unit controls the activation of the laser omitting the prohibited regions and allowing the process to continue without delay in the rest of the regions. This allows the laser to always be ready but to act only on the regions in which treatment must be applied.

Sectioning and taking of measurements by the optical module are performed continuously in a coordinated and independent manner by means of the central processing unit. Said unit updates the information received from the optical module to again determine the surface of the tissue dynamically during the sectioning procedure.

Therefore, the invention proposes for the laser and the optical module to act simultaneously, this feature being contrary to the teachings of the state of the art. The laser produces effects on the tissues which worsen the measurements taken by the optical module, so the trend up until now was to prevent the simultaneous use thereof. For example, sectioning with a laser leads to the appearance of smoke, bone dust, vibrations, or sparks which alter the measurements of the optical module. Additionally, the continuous or cyclic application of mist, irrigation, blowing, suction, or any combination of these operations for the purpose of ensuring the cooling and cleaning of the surgical area can also cause disturbances in the measurements taken by the optical module. However, the device of the invention only requires determining the surface of the tissue and said determination is robust even in the presence of the operational sectioning laser and of cleaning and cooling fluids; therefore, the impact of the alterations caused by the actuation of the laser on the measurements of the optical module does not prevent the robust identification of the shape of the surface of the tissue, and advantageously the times of the procedure are considerably reduced.

In one embodiment, the central processing unit is further configured for deactivating the laser emitter if, in the numerical model, at least one of the positions of the points of the straight line, representing the laser beam, located between the intersection of said straight line with the surface of the tissue and said intersection plus a distance equal to the sectioning depth, coincides with the position of at least one point of a prohibited region.

In this embodiment, the central processing unit estimates, in accordance with the numerical model, the position of a segment of points of the straight line, representing the laser beam, and checks if at least one of the points of said segment is within a prohibited region, in which case it deactivates the laser. Otherwise, the central processing unit activates the laser.

This segment comprises points located between the intersection of the straight line, representing the laser beam, with the surface of the tissue and said intersection plus a distance equal to the sectioning depth.

In one embodiment, the central processing unit is further configured for deactivating the laser emitter if, in the numerical model, none of the positions of the points of the straight line, representing the laser beam, coincides with the position of a point of the surface of the tissue.

For safety purposes, the central processing unit deactivates the laser in a specific position if the laser is not going to intersect with the surface of the target tissue in said position. For example, if the laser is positioned by mistake outside the surgical region, it will not strike a target tissue when activated, rather it may damage other tissues of the patient that should not be treated or even cause harm to the medical personnel.

The option of the optical module not having detected any tissue because the device has been turned on ahead of time and the patient has yet to be positioned on the operating table, for example, or simply because a failure has occurred in the optical module, is also contemplated in this embodiment. Under these circumstances, laser sectioning must be stopped to prevent an accident from happening.

In one embodiment, the at least one reference surface is:
- a boundary surface demarcating the end of the tissue of the region; or
- a boundary surface demarcating the start of a different tissue with respect to the tissue of the region the surface of which has been determined by the optical module, said different tissue being located at a greater depth than the tissue of the region; or
- a boundary surface demarcating the end of a different tissue with respect to the tissue of the region the surface of which has been determined by the optical module, said different tissue being located at a greater depth than the tissue of the region; or
- a combination of any of the foregoing.

As mentioned, the reference surface or surfaces are defined taking into consideration different criteria. In this embodiment, the reference surfaces are boundary surfaces demarcating the end or start of a tissue, whether the tissue is a tissue the surface of which has been determined by the optical module, referred to as predominant tissue, or a tissue that is adjacent thereto.

For example, in a spine surgery, the region in which the laser will perform sectioning will comprise a mix of tissues consisting of at least one vertebra, soft tissue, vessels, and other adjacent or underlying structures, such as the dura mater which protects the dural sac surrounding the spinal cord and the spinal nerves. In this case, at the start of the surgery, the predominant tissue can be the vertebra the surface of which has been determined by the optical module. A possible reference surface is the end of said vertebra. Alternatively or simultaneously, the reference surface or other reference surfaces can be surfaces demarcating the start or end of any soft tissue or of the nerves adjacent to the vertebra. In another more advanced phase of the surgery, the predominant tissue can be the yellow ligament, and a possible reference surface is the end of the yellow ligament or the start of the dural sac.

The central processing unit defines these boundary surfaces based on the information received about the anatomy present in the surgical field. Said information may come from preoperative images, and/or intraoperative images, and/or from the measurements taken by the optical module.

In one embodiment, the at least one reference surface is determined by means of a preoperative image, preferably by means of a magnetic resonance image, computerized axial tomography image, or fluoroscopy image.

The anatomy of the patient who needs surgery is known as a result of one or more medical imaging techniques, typically magnetic resonance, computerized axial tomography, or fluoroscopy performed before and/or during the course of an operation. This plan may indicate that certain elements of the volume do not have to be treated because they may belong, for example, to a critical structure such as the dural sac, a nerve, or a blood vessel.

This image is processed and segmented to only define the volume of the predominant tissue of interest. As a result, the boundaries of the predominant tissue and of the adjacent tissues are duly differentiated and this information is transformed by the central processing unit into at least one reference surface.

Alternatively or to complement the preceding information, the optical module can also determine the surface or surfaces demarcating the tissues from one another so that the central processing unit will be able define the reference surface.

With said reference surface or surfaces, the tissue or tissues which can be sectioned with the laser are demarcated from those which cannot be sectioned, thereby assuring the safety of the sectioning.

In one embodiment, the at least one reference surface determined by means of a preoperative image is a boundary surface demarcating the end of the bone tissue of the region.

In certain types of surgery, like the aforementioned spine surgery, the target tissue is the bone. Specifically, osteotomy or bone removal for laminectomies and laminotomies is a common phase in decompression and stabilization procedures. By means of a preoperative image, the boundaries of this type of tissue with respect to the adjacent tissues, such as soft tissues such as the yellow ligament, dural sac, and nerves, can be visualized.

Therefore, given that sectioning only has to be performed on the vertebra in this type of procedure, the definition of a reference surface as a boundary surface demarcating the end of said vertebra is a highly reliable safety criterion to prevent the tissues adjacent thereto from being affected by the sectioning.

After the osteotomy of one or more parts of the vertebra, another common phase of the aforementioned spine surgery is the removal of soft tissues located between the bone and the dural sac, typically the yellow ligament or ligamentum flavum, for the purpose of decompressing the nerves and removing canal stenosis, releasing them from the pressure source which causes pain. In this procedure, the end of the yellow ligament, the surface of the dural sac, or any other combination of the initial or final surfaces of the tissues present in the anatomical area of interest, can be used as a reference surface.

In one embodiment, the at least one reference surface is a flat surface essentially parallel to a focal plane of the laser emitter and/or to a focal plane of the optical module.

In this embodiment, the reference surface or at least one of the reference surfaces is a flat surface defining an allowed maximum sectioning level. This surface is substantially flat and parallel to a focal plane, whether the focal plane of the laser or the focal plane of the optical module. Preferably, both focal planes coincide with one another. Throughout the document, focal plane will be understood to mean the plane perpendicular to the optical axis in which the laser emitter and/or the optical module reach their optimal spatial resolution or focus.

Preferably, this maximum level is chosen by the surgeon and received by the central processing unit which converts the information into the reference surface. Furthermore, this maximum level can be dynamic, i.e., the depth thereof can be gradually updated as the surgical intervention progresses. Throughout the document, when the term surgeon is mentioned, it can be understood to mean any user authorized for intervening in the operation or healthcare personnel.

Preferably, the sectioning laser gradually sweeps across the biological tissue until it levels out the surface, taking into account a margin of tolerances beyond which it is considered that the surface has been leveled out successfully. For reasons of safety, this progression and leveling out in tissue sectioning is performed at all times without encroaching upon the defined flat surface. According to this mode of actuation, the laser beam acts more frequently on points of the surface having a greater height.

Additionally, this type of reference surface provides several relevant technical advantages derived from the fact that both the sectioning laser and the optical module have a focal plane in which the measurement is optimal.

On one hand, when the tissue of the region has been leveled out, the measurements of the optical module are obtained in favorable conditions since said optical module can be optimally focused without any height irregularities which may degrade the measurements or produce shaded areas, thereby performing the measurement of the surface of the sample in the most favorable conditions. Moreover, the leveling out of the tissue also allows the laser to focus more optimally on the tissue and to encounter a surface free of obstacles, which translates into a more efficient sectioning. Lastly, providing a leveled-out sectioning area facilitates other tasks which, though not a part of the surgery as such, are strictly necessary for the success thereof, such as the task of performing irrigation during the operation to keep the surgical field clean and to prevent thermal damage.

In one embodiment, the at least one reference surface is a surface with a maximum depth determined from the surface of the tissue.

In this embodiment, the reference surface or one of the reference surfaces is a surface with a depth indicating the allowed maximum sectioning depth, point by point, with respect to the surface of the tissue determined by the optical module.

This surface with a depth can be defined with respect to the surface of the tissue of the region initially determined by the optical module or at any other time of the surgery in which an update of said surface of the tissue has taken place.

Advantageously, this type of reference surface constitutes a safety means of the device preventing the tissue from being sectioned at a depth greater than that defined by the central processing unit, thereby preventing the sectioning of tissues other than the target tissue.

In one embodiment, the at least one reference surface is
  a boundary surface demarcating the end of the tissue of the region; and/or
  a boundary surface demarcating the start of a different tissue with respect to the tissue of the region the surface of which has been determined by the optical module, said different tissue being located at a greater depth than the tissue of the region; and/or
  a boundary surface demarcating the end of a different tissue with respect to the tissue of the region the surface of which has been determined by the optical module, said different tissue being located at a greater depth than the tissue of the region; and/or
  a flat surface essentially parallel to a focal plane of the laser emitter and/or to a focal plane of the optical module; and/or
  a surface with a maximum depth determined from the surface of the tissue.

The reference surface can be an individual surface, according to any of the surfaces defined in the preceding embodiments, or a set of reference surfaces that must be taken into account simultaneously. Therefore, the device according to the invention contemplates a large variety of safety options which can be adapted to each particular surgery.

In one embodiment, the central processing unit defines the at least one reference surface with a safety margin.

Despite the fact that sectioning with a laser is much more precise than sectioning with conventional surgical instruments, the device of the invention contemplates that all the reference surfaces have a safety margin to even further increase the safety of the method, preventing the sectioning of non-target tissues at all times.

Furthermore, the safety margins can be dynamic, i.e., they can gradually change throughout the surgical intervention.

Safety margin is understood to mean a pre-established distance such that if a laser beam must not exceed a reference surface, the point determining whether or not the reference surface is exceeded is a point spaced by the pre-established distance so as to prevent reaching said reference surface. In this case, the safety margin is equivalent to considering that the reference surface has been moved closer to the emission source by the pre-established distance.

In one embodiment, the central processing unit comprises input means for inputting the definition of the safety margins of the at least one reference surface.

The margins can be selected by the surgeon or medical personnel responsible for the operation, who transmits the values of these margins to the central processing unit through input means. In turn, the central processing unit defines or updates the reference surface or surfaces taking into account said margins in the numerical model.

In one embodiment, the optical module comprises an optical coherence tomography OCT system.

Throughout this document, OCT system will be understood to mean an optical system capable of determining the volume of the region of biological tissues to be sectioned by illuminating said region with a partially coherent source, typically a superluminescent diode or a scanning source. Based on this information obtained by the OCT system, the optical module identifies the surface of the target tissue or the predominant tissue.

In one embodiment, the optical coherence tomography system is a polarization-sensitive optical coherence tomography PS-OCT system.

More particularly, the OCT system of the optical module being a polarization-sensitive optical coherence tomography PS-OCT system is contemplated in this embodiment. Systems of this type are characterized in that their measurements take into account that tissues can modify the polarization state of the light they reflect.

Advantageously, systems of this type offer extremely robust measurements since they perform the post-processing of the light reflected by the tissues, such that they cause the reflectance or intensity signal to become insensitive to the polarization variations caused by said tissues, providing an optimal contrast regardless of the polarimetric effects produced in the tissue. This allows determining the surface of the tissue in a robust manner. Additionally, tissues which cannot be distinguished by means of OCT can be distinguished in a precise manner with PS-OCT, taking into consideration the different response thereof to polarization, thereby identifying prohibited areas which would not have been identified otherwise.

As mentioned, preferably, the sectioning laser gradually sweeps across the biological tissue until it levels out the surface. Under these circumstances, the system of the optical module, for example the PS-OCT system, takes measurements in optimal conditions because the leveling of the surface allows the tissue to be located in the focal plane of said system. Similarly, the laser emitter acts in optimal conditions when the leveled-out surface of the tissue is located in its focal plane.

In one embodiment, the optical module comprises a system of the:
  structured light type;
  stereo pair type; or
  optoacoustic tomography type.

Alternatively to the OCT and PS-OCT systems, the optical module may comprise another type of optical systems (structured light or stereo pair) or optoacoustic systems (optoacoustic tomography) such as those mentioned above.

In particular, a structured light system illuminates the tissues using typically infrared light with a projector that makes a spatial pattern, for example, a checkered pattern. The light pattern is deformed according to the shape of the surface, so if the pattern on a flat surface is known, the shape of the surface can be inferred from the capture of the deformed pattern.

A stereo pair system illuminates the tissue typically with an infrared light source and reconstructs the volume of the tissues by means of stereoscopic techniques.

In turn, the optoacoustic tomography system illuminates the tissues with laser and takes measurements with an ultrasonic transducer.

In one embodiment, the laser emitter comprises a scanner which allows changing the direction of the beam so as to aim it at different points of the region.

This scanner allows the laser to sweep across a previously defined scanning area or pattern. Preferably, said pattern is uniform. In one example, from the perspective of a surgeon performing an operation, the pattern is made from the left side of the surgeon to the right side and from top to bottom.

Solutions in which sectioning is established specifically in each position, such that the laser does not progress to the next position until the sectioning in one position has been completed, are known in the state of the art. However, in the context of the invention, solutions of this type are not optimal for the operation of the optical module since the measurements thereof may become extremely difficult, and even impossible, in deep and narrow individual holes or in the presence of complicated angles or shapes on the surface of the tissue. Therefore, gradually progressing in the entire region and not at a single point facilitates the measurements of the optical module, and therefore the definition of the surface of the tissue throughout the entire surgery. Additionally, visualization of the surgical field by the surgeon is facilitated and the phase of the surgery closest to critical tissues is reached gradually, approaching them in unison, allowing improved safety.

During that process which is performed in a repetitive and continuous manner, the laser can interact with areas that do not have to be treated; i.e., those referred to above as prohibited areas. Preferably, in such situations, the scanner allows the laser to be redirected towards the regions with target tissues, omitting the prohibited areas. As a result, the laser does not cool down and continues the sectioning procedure in optimal conditions without delay, allowing the time needed for performing sectioning to be minimized.

Alternatively, the scanner allows the laser to continue the predefined pattern by sweeping across the prohibited areas but the central processing unit prevents the laser from being activated, thereby preventing it from sectioning non-target tissues.

In one embodiment, the central processing unit is adapted for carrying out a continuous scanning of the laser beam emitted by the laser emitter over the region until reaching the at least one reference surface.

In this embodiment, the central processing unit allows the scanning of the laser until reaching the reference surface or one of the reference surfaces.

For example, when the reference surface is a flat surface defining a maximum sectioning level, the central processing unit allows the scanning of the laser until reaching said maximum level. If, at this point, the depth of the level is to be increased, the central processing unit will proceed to resume the scanning of the laser.

In another example, when the reference surface is a boundary surface demarcating the end of a bone, the central processing unit allows the scanning of the laser until reaching the end surface of the bone. In a more particular example in which a safety margin is furthermore imposed, the central processing unit allows the scanning of the laser until a remaining thickness equal to said safety margin remains in the entire bone.

In one embodiment, the optical module comprises an optical source and a scanner which allows changing the direction of the optical source so as to aim it at different points of the region.

In this embodiment, the optical module comprises an OCT system, a PS-OCT system, or an optoacoustic tomography system which, in turn, comprise an optical source. To scan the region of interest, the optical module further comprises a scanner which allows focusing said source on different points of the region.

Advantageously, as sectioning progresses during the surgery, the source of the optical module is focused on the points of the tissue in which the new surface is located so that the central processing unit will be able to precisely redefine said surface in the numerical model.

In one embodiment, the central processing unit is adapted for carrying out a continuous scanning of the optical source of the optical module over the region.

In this more particular embodiment, the central processing unit controls the aforementioned scanning of the optical source.

In one embodiment, the control of the scanning established by the laser emitter and the scanning established by the optical module are independent.

Although the laser emitter scans and the optical module scans are controlled by the central processing unit, both scans are independent of one another. The parameters defining each of said scans, such as speed, are therefore completely independent of one another, so said scans can be stopped or modified without the other scan being affected.

Scanning by the optical module may require, for example, a smaller scanning frequency so that information about the tissue is suitably updated.

In one embodiment, the scanning of the optical source of the optical module over the region is performed when an obsolescence criterion selected from the following is met:
  after a pre-established time period has elapsed,
  prior to the activation or deactivation of the laser emitter by the central processing unit.

As set forth above, the sectioning paths and the measurements of the optical module are carried out independently, so they do not have to be in line with one another.

Although the optical module takes measurements continuously, an error may occur when the module scans over the region of interest or the measurements may be taken in excessively long time instants. Therefore, the information on which the numerical model is based in a given time instant may be outdated, and this may lead to the tissues being sectioned erroneously, putting the surgery at risk.

To prevent such situations, the device provides an update of the measurements taken by the optical module in critical situations, particularly when a previously predefined time period has elapsed, thereby preventing any problem when refreshing the taking of measurements, and before the central processing unit activates or deactivates the laser emitter, such that it is ensured that a tissue, the information of which is updated in the numerical model, is being sectioned or is not being section.

In one embodiment, the numerical model generated by the central processing unit, the at least one flat surface is established progressively in a plurality of depth levels with respect to the focal plane of the laser emitter and/or the focal plane of the optical module, such that the at least one flat surface changes to a greater depth when the surface of the tissue has descended to the depth of said flat surface as a result of the action of the laser of the laser emitter.

When at least one of the reference surfaces is a flat surface parallel to a focal plane, i.e., the focal plane of the laser emitter and/or the focal plane of the optical module, said surface is defined at a specific depth. This depth can gradually progress as the laser reaches the flat surface defined at a given time such that the flat surface is updated at a depth greater than the preceding one.

Therefore, a plurality of levels at different depths which allows sectioning to be performed gradually by segments where safety is assured are defined.

The plurality of levels can be fixed, i.e., predefined before starting the surgery, or dynamic, i.e., the flat surface is gradually updated as the surgery progresses. In a particular example, the difference in depths between the consecutive levels is constant. In another example, the difference in depths between the consecutive levels is variable. In another example, the surgeon decides on the new depth of the flat surface during the surgery and enters its value through input means in the central processing unit which converts said information into the new updated flat surface and assigns it to the numerical model.

In one embodiment, the central processing unit comprises input means for inputting the definition of the at least one reference surface which are assigned to the numerical model.

It has been mentioned throughout the document that the surgeon or medical personnel can make different decisions relating to the reference surfaces before and during the surgical intervention. These decisions must be taken into account by the central processing unit which analyzes the received information and uses it to define the reference surfaces and to assign said reference surfaces to the numerical model.

Preferably, the input means are configured with an interface allowing interaction between the central processing unit and the surgeon, medical personnel, or user.

In one embodiment, the central processing unit comprises input means for inputting the definition of a region to be avoided, the shape of which is assigned to the numerical model; and the central processing unit is further configured for deactivating the laser emitter if, in the numerical model, at least one of the positions of the points of the straight line, representing the laser beam, located between the intersection of said straight line with the surface of the tissue and said intersection plus a distance equal to the sectioning depth, coincides with the position of at least one point of the region to be avoided.

In addition to the prohibited regions, for safety reasons, the user, surgeon, or medical personnel can decide on what other type of specific regions cannot be sectioned with the laser before or during a surgery, for example, when the existence of a critical structure which is not within a prohibited region is identified during the surgery.

For these situations, the central processing unit comprises additional input means from which the user can define a region to be avoided, with region to be avoided being understood to mean a particular region that cannot be sectioned with the laser. Preferably, these input means are an interface.

In a preferred example, the region to be avoided is defined in a plan view of the surgical field, sectioning at any depth thus being prohibited at all the points the "x" and "y" coordinates of which belong to the defined region. The "x" and "y" coordinates must be interpreted generically as the coordinates with which specific points of a surface are identified, regardless of the manner in which the surface has been parameterized. In a particular example in which a Cartesian coordinate system is used, the "x" and "y" coordinates correspond to the x and y axes.

This information is received by the central processing unit which is responsible for processing it to assign the shape of the region to be avoided to the numerical model. Additionally, the central processing unit is configured for deactivating the laser emitter if the beam thereof, in accordance with the established sectioning depth, penetrates the region to be avoided.

In one embodiment, the device comprises surgical field display means, preferably a screen showing an RGB video image.

To offer visual information to the user at all times during the surgical intervention, the device comprises these display means. In a preferred example, the display means are a screen or monitor showing the surgeon a video image of the surgical field in a plan view and particularly an RGB image. RGB image must be understood to mean an image the colors of which can be defined by means of the standard RGB color model.

Furthermore, the display means advantageously help the user or surgeon in choosing the region to be avoided, if it is considered necessary. That region to be avoided is drawn by the user in the context of the image shown on the display means, preferably an RGB video showing the surgical field in a plan view. In these cases, sectioning at any depth is prohibited at all the points the 'x' and 'y' coordinates of which belong to the region defined from the image shown on the display means.

In one embodiment, the surgical field display means further show information about the distance from each point of the surface of the tissue to the at least one reference surface.

In order to have an additional source providing visual information about the approach towards the target of the surgery, in this embodiment, the surgeon is informed of the distance from each point of the surface of the tissue to the reference surface. If there is more than one reference surface, the distance will be calculated up to the reference surface closest to each point. This additional information is imposed on the image shown in the surgical field display means.

The central processing unit calculates distances in accordance with the numerical model and shows said distances through the surgical field display means.

In one embodiment, the central processing unit is further configured so that, during a sectioning process while the laser emitter scans a set of points of the region, every time the sequence of points reaches a point where the emission of the laser emitter is hindered, the laser emitter is positioned in the next point at which emission is allowed without stopping the emission of the laser beam.

To prevent a delay in the procedure, when the laser of the device is to strike a point on which sectioning must not be performed, the central processing unit redirects the laser towards another region that does comprise the target tissues, i.e., towards another region on which sectioning must be performed. Preferably, the laser is redirected by means of a scanner comprised in the optical module.

According to this embodiment, advantageously, not only are times in which the laser is inactive avoided, but rather by skipping to another point where it can continue working, the laser will not cool down and will remain in optimal operating conditions.

Alternatively, the central processing unit orders the laser emitter to sweep across all the points of the region but only allows its activation at those points in which sectioning is allowed.

In one embodiment, the central processing unit is further configured for defining a function representing a scalar representative of the temperature level in a set of points of the region with a specific pattern, wherein:

the function initially takes a pre-established reference value;

every time the laser emitter strikes a point of the pattern, the function is increased at that point by a first pre-established incremental value;

the values of all the points are reduced at every pre-established time period by a second pre-established incremental value;

for each point of the pattern, if it exceeds a pre-established threshold value, said point is assigned in the numerical model as the point where sectioning is not allowed as long as it remains above said threshold value.

When the size of the sectioning region is very small, the situation in which the laser acts on these regions in a largely continuous manner and thermally damages these regions may occur. Therefore, although the process can start with a wide actuation region, increasingly larger prohibited areas, and optionally areas to be avoided, may arise during sectioning. The regions in which sectioning will be performed therefore become increasingly smaller and the laser passes through said regions more and more often, increasing the power per unit of surface in the process. When this power exceeds a specific threshold, the tissue starts to sustain burns.

In the state of the art, to prevent laser sectioning from causing any thermal damage due to tissue heating, there is a need to cool the sectioning area by means of irrigation or mist. As a result, the trend up until now is not to use the laser emitter and the optical module simultaneously, but rather the sectioning of the tissue and measurements of the optical module are performed in an alternating manner. However, as mentioned throughout the document, the invention does contemplate the simultaneous use of the laser and the optical module as an embodiment.

The device according to this embodiment contemplates regulating the power per unit of surface of the laser so that it does not exceed a predefined threshold. This threshold can be a dynamic threshold or can gradually change throughout the surgical intervention. In one example, the user, surgeon, or medical personnel selects the threshold at a given time of the operation and enters same through input means of the central processing unit which are preferably an interface.

This thermal protection is based on a simplified tissue temperature model, taking into account the point-by-point tissue heating and cooling having the number of laser pulses that is allowed per unit of time.

In this model, a scalar reflective of the temperature of a point of the tissue is defined. Every time the laser is fired, this scalar increases by a fixed incremental amount such that, if the predetermined threshold value is exceeded, the numerical model contemplates said point being a point at which sectioning is not allowed as long as the associated temperature scalar remains above the threshold.

As mentioned, the model also contemplates tissue cooling, so the scalar, in each point of the tissue, decreases by a fixed decremental amount (equal to or different from the fixed incremental amount) when a predetermined time period has elapsed. This time period can be a fixed or dynamic time period during the surgery. Furthermore, it can be selected at a given time of the surgery by the surgeon or medical personnel, who will enter the value in the central processing unit through input means, preferably an interface.

In one embodiment, the central processing unit is further configured so that, during a sectioning process while the laser emitter scans a set of points of the region, the points where the sectioning depth is smaller than others are given priority in the scanning sequence so as to compensate for the sectioning depth.

As set forth above, one way of laser sectioning a target region can be performed by means of a control mode which regulates the activation of the laser to achieve a section that always has a flat bottom. Therefore, during the sectioning process, there will be regions that are deeper than others.

To achieve the objective of leveling out the bottom of the section, in this embodiment, it is contemplated that the central processing unit is configured to give priority to the shallower points, such that it deactivates the laser at the deeper points or areas and activates it at more superficial points or areas. According to another embodiment, skipping from one point to another is performed without deactivating the laser, but striking those points with a greater height more times. In this manner, the superficial areas become increasingly deeper while the deep areas remain unchanged until all the points end up having the same level.

In one embodiment, the central processing unit comprises means for stopping the emission of the laser emitter adapted for stopping the emission of the laser emitter when it is operating.

The device of the invention also contemplates an option for stopping the actuation of the laser under any circumstance, even though no other safety criterion defined above is met.

To that end, the central processing unit receives the stop order, which will preferably have been issued by the user or surgeon, from the outside. Advantageously, sectioning safety is assured when, for any reason, the medical personnel considers that the sectioning must be stopped.

In one embodiment, the device further comprises a fluid management unit adapted for providing, in the operating mode, a flow of a gas, or of a liquid, or of a mist with liquid particles in gas, in a region containing the region of biological tissue on which the laser emitter acts.

The tissues sectioned by the device tend to bleed continuously and the sectioning operation itself also continuously generates particles and solid residues that must be removed from the laser actuation area.

In this embodiment, in addition to laser sectioning, the device has cleaning capacity. To that end, it comprises a fluid management unit providing a flow of gas, liquid, or a mist capable of entraining unwanted elements present in a region containing the region of tissues to be sectioned by the laser emitter.

Preferably, the flow of gas or liquid or the mist is provided through a conduit connecting the fluid management unit with the surgical region.

Advantageously, on one hand, the laser can act on a tissue area which is free of blood and/or unwanted particles that may affect sectioning precision, and on the other, the accuracy of the measurements of the optical module are not affected, where the actual surface of the target tissue can be determined free of these unwanted elements.

A second inventive aspect provides the use of the device of the first inventive aspect in a minimally invasive robot-assisted surgical procedure.

DESCRIPTION OF THE DRAWINGS

These and other features and advantages of the invention will become more apparent based on the following detailed description of a preferred embodiment given solely by way of illustrative and non-limiting example with reference to the attached figures.

DETAILED DESCRIPTION OF THE INVENTION

Figure 1:
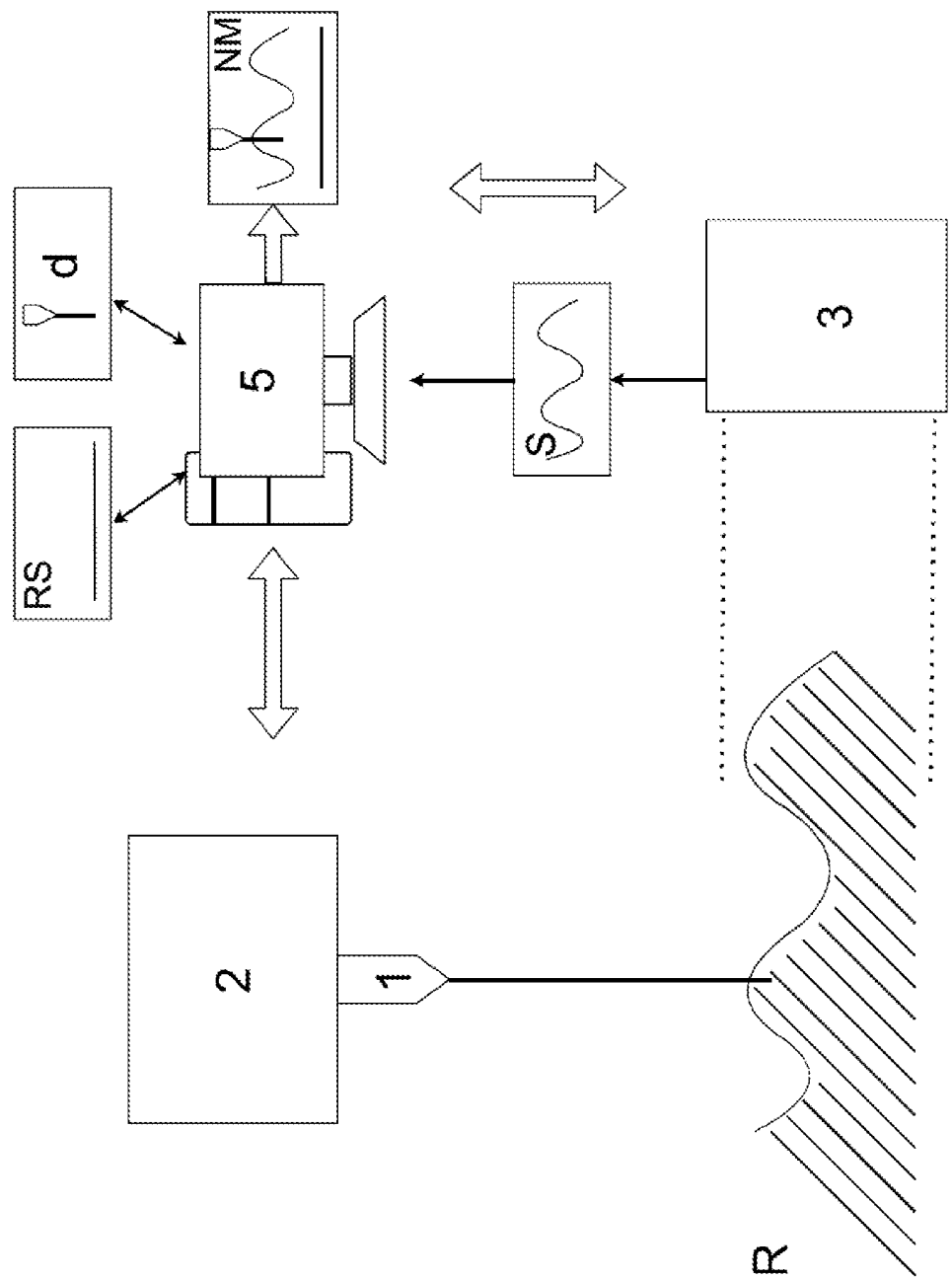
FIG. 1 shows a general diagram of the device according to an embodiment of the invention.

FIG. 1 shows a general diagram of the biological tissue sectioning device for sectioning biological tissues depicted in this figure by means of parallel lines. The device comprises a laser emitter (1) configured for sectioning said tissues in a region (R), the activation and deactivation of which is ordered by a controller (2).

In one embodiment, the laser emitter (1) comprises a scanner which allows changing the direction of the beam so as to aim it at different points of the region (R).

The device further comprises an optical module (3) capable of detecting the surface(S) of the tissue of the region (R). Preferably, the optical module (3) comprises an optical or optoacoustic system taking a series of measurements subsequently processed by computational means to determine the surface(S) of the tissue.

In a preferred example, the optical module (3) comprises an optical coherence tomography system (OCT), which can be a polarization-sensitive optical coherence tomography (PS-OCT) system. Other examples of optical systems of the optical module (3) are of the structured light or stereo pair type. Another example of the optoacoustic system of the optical module (3) is an optoacoustic tomography system.

In one embodiment, the optical module (3) further comprises an optical source and a scanner which allows changing the direction of the optical source so as to aim it at different points of the region (R).

The device further comprises a central processing unit (5) in communication with the controller (2) and the optical module (3). On one hand, it sends orders for activating and deactivating the laser to the controller (2), and on the other hand, it receives information from the optical module (3) and processes it. The central processing unit (5) generates a numerical model (NM) of the region (R) comprising at least the shape of the surface(S) of the region (R) determined by the optical module (3), the direction of the laser beam in which the laser emitter (1) is oriented, and the shape of one or more reference surfaces (RS).

The reference surface or surfaces (RS) are defined by the processing unit (5) itself. These surfaces (RS) demarcate the surface of a prohibited region of the tissues in which sectioning is prohibited for several reasons, for example, because said region contains a critical tissue such as a nerve or a blood vessel.

Moreover, the central processing unit (5) defines a sectioning depth (d) of the laser emitter (1) which can be fixed or varied throughout the entire surgical intervention. Preferably, the sectioning depth (d) can be selected.

Based on the generated numerical model (NM), the central processing unit (5) estimates the position of the point of the straight line, representing the laser beam, spaced from the intersection of said straight line with the surface(S) of the tissue by a distance equal to the sectioning depth (d). If the estimated position indicates that the point is located outside a prohibited region, the central processing unit (5) activates the laser emitter (1) through the controller (2), and in contrast, the central processing unit deactivates the laser emitter if said point is within the prohibited region.

Alternatively or additionally, based on the generated numerical model (NM), the central processing unit (5) estimates the position of the points of the straight line, representing the laser beam, positioned from the intersection of said straight line with the surface(S) of the tissue to said intersection plus a distance equal to the sectioning depth (d). If the estimated positions of said points do not coincide with the points of a prohibited region, the central processing unit (5) activates the laser emitter (1) through the controller (2), and in contrast, the central processing unit deactivates the laser emitter if the position of at least one of the points coincides with at least one point of the prohibited region.

The central processing unit (5) defines the reference surface or surfaces (RS) based on several criteria.

Criterion 1: boundary surface demarcating the start or end of a tissue. This tissue can be the tissue the surface(S) of which has been determined by the optical module (3), i.e., the predominant tissue, or a tissue adjacent thereto.

Criterion 2: flat surface essentially parallel to a focal plane of the laser emitter (1) and/or to a focal plane of the optical module (3) establishing a maximum sectioning level.

Criterion 3: surface with a maximum depth estimated, point by point, from the surface(S) of the tissue determined by the optical module (3).

These reference surfaces (RS) can be dynamic surfaces, i.e., they may change throughout the surgical intervention. For example, a flat surface establishing a maximum sectioning level at the start of the operation can be updated to a greater depth as sectioning progresses. In another example, since the surface(S) of the tissue gradually varies throughout the operation, different surfaces with a maximum depth can be progressively defined.

The central processing unit (5) defines these reference surfaces (RS) based on preoperative information, on the measurement of the optical module (3) itself, and/or on decisions made by the medical personnel. Once it has defined said reference surfaces, it assigns them to the generated numerical model (NM).

Furthermore, in order to increase safety during sectioning, the device contemplates the inclusion for said reference surfaces (RS) of safety margins which can be fixed or which vary throughout the surgical intervention. Preferably, the central processing unit (5) comprises input means for inputting the definition of safety margins, with the medical personnel being responsible for entering said margins through an interface.

Figure 2:
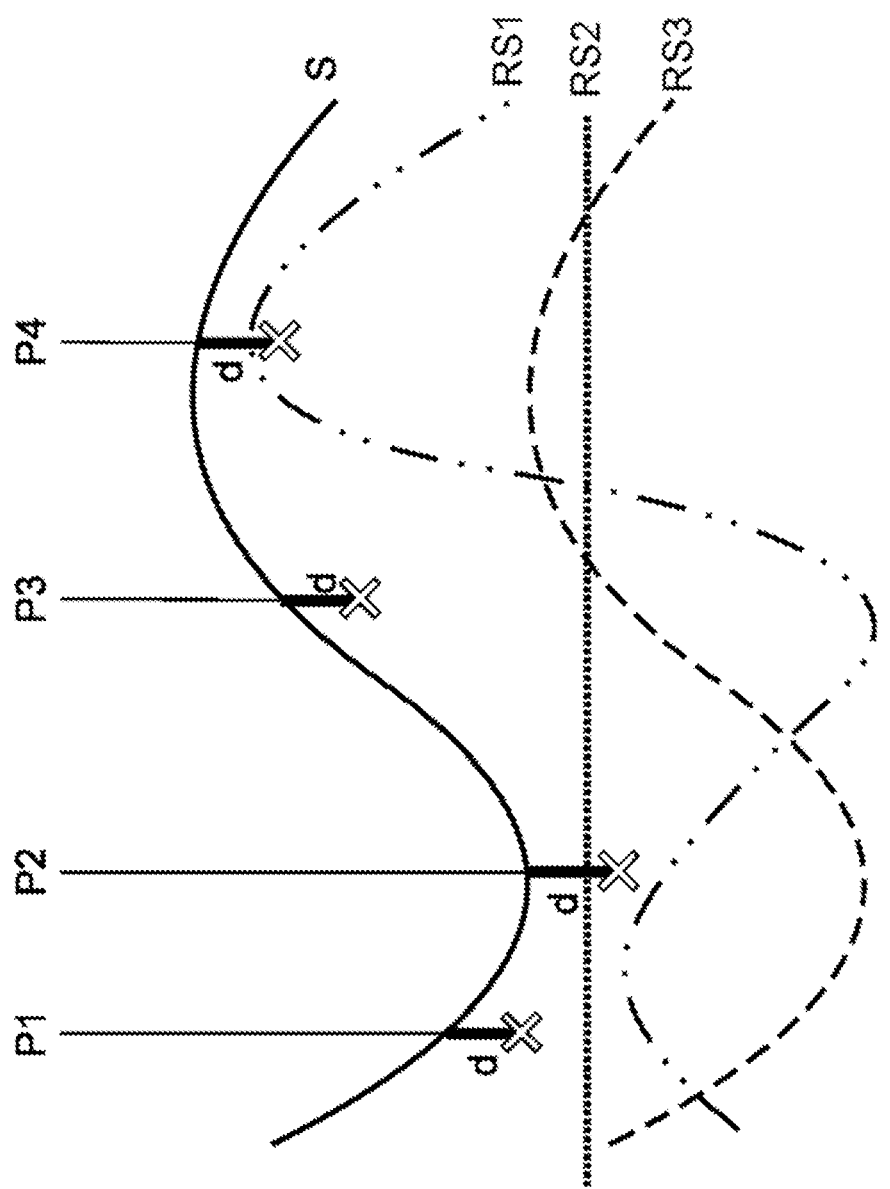
FIG. 2 shows a diagram of a section of the surface of the tissue determined by the optical module together with three different reference surfaces.

FIG. 2 shows an exemplary surface(S) of the tissue of the region (R) determined by the optical module (3) and three reference surfaces (RS1-RS3) defined in accordance with three different criteria.

Reference surface RS1 is a surface demarcating the end of the predominant tissue, for example, the end of a vertebra in spine surgery. In this example of FIG. 2, the central processing unit (5) defines this surface RS1 and assigns it to the numerical model (NM) based on preoperative images, such as images acquired by means of magnetic resonance, computerized axial tomography, or fluoroscopy. In an alternative example, the central processing unit (5) defines this surface RS1 and assigns it to the numerical model (NM) based on the measurements taken by the optical or optoacoustic system of the optical module (3).

Reference surface RS2 is a flat surface with a maximum level. In this example of FIG. 2, the depth of this reference surface RS2 has been defined by the surgeon at the start of the surgery. The value of the depth decided by the surgeon is received by the central processing unit (5) through an interface and said unit (5) then processes the information to define reference surface RS2 and assigns it to the numerical model (NM).

Reference surface RS3 is a surface with a maximum depth defined, point by point, with respect to the surface(S) of the tissue determined at the start of the surgical intervention by the optical module (3). The central processing unit (5) receives the surface(S) of the tissue from the optical module (3), processes the information, defines the surface with a maximum depth RS3, and assigns it to the numerical model (NM).

Additionally, reference surfaces RS2 and RS3 will gradually change throughout the surgical intervention. On one hand, the surgeon will be able to enter through the interface new values of the depth for the new flat surfaces RS2 that will then be processed by the central processing unit (5) to define and assign said surfaces to the numerical model (NM). Moreover, taking into account that the surface(S) of the tissue evolves as the sectioning procedure progresses, the central processing unit (5) will be able to define new surfaces with a maximum depth RS3 as it gradually receives updates concerning the surface(S) of the tissue from the optical module (3), subsequently assigning said new surfaces with a maximum depth RS3 to the numerical model (NM).

Additionally, FIG. 2 shows a series of points of the tissue (P1-P4) on which the laser beam strikes, with the central processing unit (5) being responsible for determining whether or not the laser must be activated in each case. To that end, as mentioned, the central processing unit (5) estimates the position of the point of the straight line, representing the laser beam, spaced from the intersection of said straight line with the surface(S) of the tissue by a distance equal to the sectioning depth (d). Said point is depicted in the figure by a cross. It is understood that the point is spaced from the intersection in the opposite direction of the laser beam source, i.e., the point located in the tissue. If the estimated position indicates that the point is located outside a prohibited region, i.e., the region below one of the reference surfaces (RS1-RS3), the central processing unit (5) activates the laser emitter (1) through the controller (2), and in contrast, the central processing unit (5) deactivates the laser emitter if said point is within a prohibited region.

Alternatively, the central processing unit (5) estimates the position of the points on the straight line, representing the laser beam, comprised between the intersection of said straight line with the surface(S) of the tissue and said intersection plus a distance equal to the sectioning depth (d). If the estimated positions indicate that the entire segment is located outside a prohibited region, i.e., the region below one of the reference surfaces (RS1-RS3), the central processing unit (5) activates the laser emitter (1) through the controller (2), and in contrast, the central processing unit (5) deactivates the laser emitter if the segment is at least partially within a prohibited region.

The state of the laser (1) at each of the aforementioned points of FIG. 2 is described below.

Point P1: laser is activated because the point is outside all the prohibited regions.

Point P2: laser is deactivated because the point is within the prohibited region defined by surface RS2.

Point P3: laser is activated because the point is outside all the prohibited regions.

Point P4: laser is deactivated because the point is within the prohibited region defined by surface RS1.

In one example, the central processing unit (5) of the device described in any of FIG. 1 or 2 is further adapted for carrying out a continuous scanning of the optical source of the optical module (3) over the region (R).

The central processing unit (5) controls the scanner allowing the source of the optical module (3) to sweep across the region (R) performing a continuous scanning. As a result, the measurements and, with them, the surface(S) of the tissue, are gradually updated in the numerical model (NM).

In a more particular example, this scanning by the optical source is performed when an obsolescence criterion of the measurements selected from the following is met:

after a pre-established time period has elapsed,
prior to the activation or deactivation of the laser emitter (1) by the central processing unit (5).

By imposing these obsolescence criteria, the device assures that the measurements of the optical module (3) will be gradually updated at least every pre-established time period and/or every time the laser is to change from the inactive to the active state (or vice versa).

In one example, the central processing unit (5) is also adapted for carrying out a continuous scanning of the laser beam emitted by the laser emitter (1) over the region (R) until reaching the at least one reference surface (RS). In a particular example, the control of the scanning established by the laser emitter (1) and the scanning established by the optical module (3) are independent.

This scanning is performed following a previously defined scanning pattern. Preferably, said pattern is uniform. In one example, from the perspective of a surgeon performing an operation, the pattern is made from the left side of the surgeon to the right side and from top to bottom.

During that process which is performed in a repetitive and continuous manner, the laser (1) can interact with areas that do not have to be treated; i.e., those referred to above as prohibited areas.

In a preferred example, the central processing unit (5) is further configured so that, during a sectioning process while the laser emitter (1) scans a set of points of the region (R), every time the sequence of points reaches a point where the emission of the laser emitter (1) is hindered, the laser emitter is positioned in the next point at which emission is allowed without stopping the emission of the laser beam.

That is, the central processing unit (5) performs control such that the laser omits the prohibited regions, with the process thus being completed without delay. The laser can be redirected towards non-prohibited regions by means of the scanner of the optical module (3).

Besides the obvious speed achieved with this method, it further presents the advantage of the laser operating in optimal conditions at all times because it is not deactivated, and therefore does not cool down.

Alternatively, the central processing unit (5) can order the laser to continue scanning the predefined pattern by sweeping across the prohibited areas but preventing the laser (1) from being activated over said areas.

In a preferred example, the sectioning laser gradually scans the biological tissue until it levels out the surface(S), taking into account a margin of tolerances beyond which it is considered that the surface has been leveled out successfully.

To achieve the objective of leveling out the bottom of the section, in one embodiment, the central processing unit (5) is further configured so that the points where the sectioning depth is smaller than others are given priority in the scanning sequence so as to compensate for the sectioning depth.

Therefore, the central processing unit (5) gives priority to shallower points, such that it deactivates the laser at the deeper points or areas, and activates it at more superficial points or area. In this manner, the superficial areas become increasingly deeper while the deep areas remain unchanged until all the points end up having the same level.

According to another embodiment, to maintain the operating conditions of the laser and to keep the laser from cooling down with deactivation, the laser remains active but skips between points with a greater height, avoiding passage through points with a smaller height.

Figure 3:
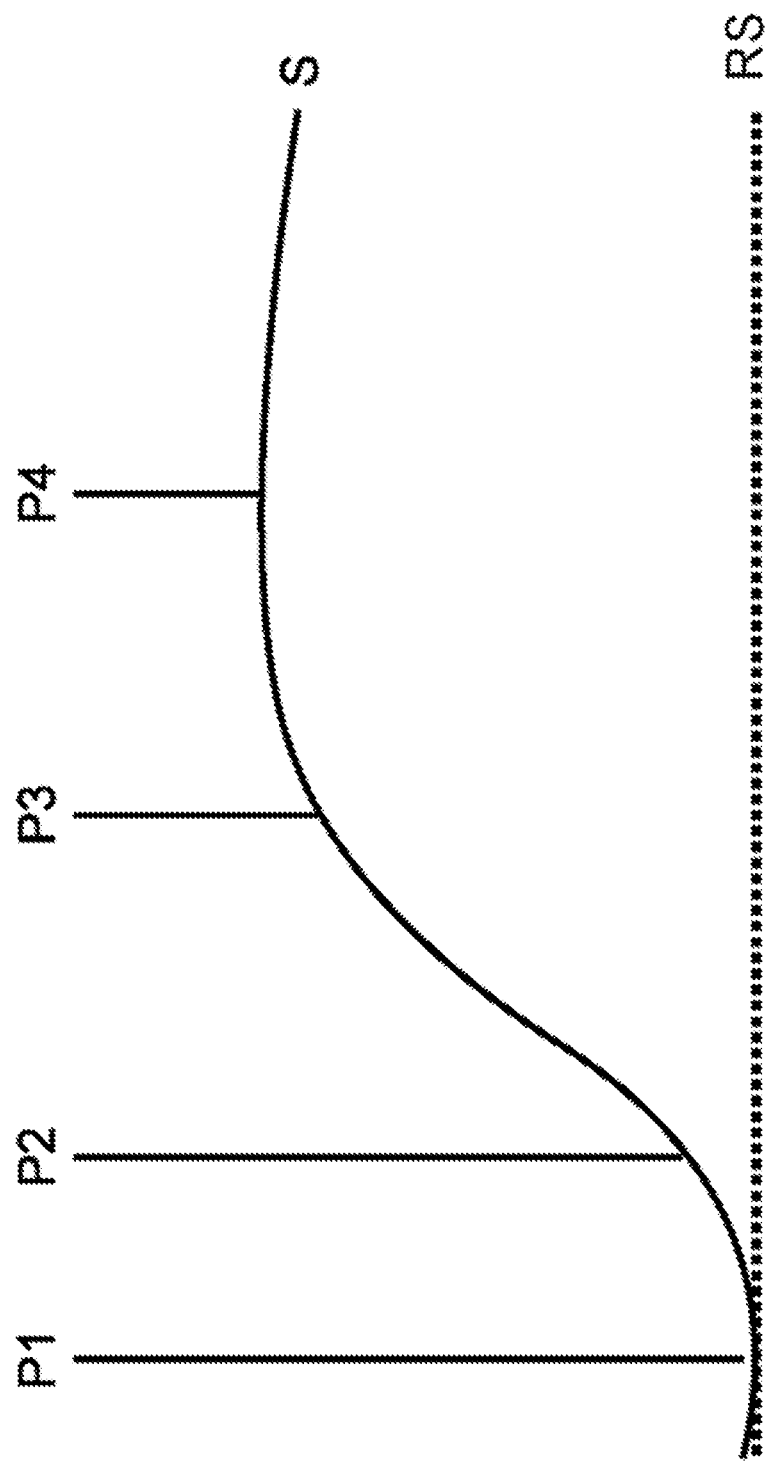
FIG. 3 shows an example of how the central processing unit prioritizes the points for sectioning over other points so as to level out the surface of the tissue.

This embodiment is illustrated in FIG. 3 which shows the positions of a set of points of the surface(S) of the tissue on which the laser (1) strikes. In this particular example, a flat reference surface (RS) defining the maximum sectioning level to be reached has been defined.

It can be seen that at point 1 the surface(S) of the tissue has reached the maximum sectioning level, whereas at points P2 to P4 the surface(S) is shallower. To achieve the objective of leveling out the section, the central processing unit (5) in this example will give priority to the sectioning at point P4 followed by points P3 and P2. For reasons of safety, this progression and leveling out in tissue sectioning is performed at all times without encroaching upon the defined flat reference surface (RS).

This flat reference surface (RS) can be established progressively in a plurality of depth levels with respect to the focal plane of the laser emitter (1) and/or the focal plane of the optical module (3), such that the at least one flat surface changes to a greater depth when the entire surface(S) of the tissue has descended to the depth of said flat surface as a result of the action of the laser of the laser emitter (1).

In one example, any of the reference surfaces (RS) can be defined by input means comprised in the central processing unit (5) for inputting the definition of the at least one reference surface (RS), the defined reference surfaces (RS) subsequently being assigned to the numerical model (NM).

Additionally, in another example, the central processing unit (5) comprises input means for inputting the definition of a region to be avoided (RA), the shape of which is assigned to the numerical model (NM). The central processing unit (5) is further configured for deactivating the laser emitter (1) if, in the numerical model (NM), at least one of the positions of the points of the straight line, representing the laser beam, located between the intersection of said straight line with the surface(S) of the tissue and said intersection plus a distance equal to the sectioning depth (d), coincides with the position of at least one point of the region to be avoided (RA).

In a particular example, the surgeon selects a region to be avoided (RA) from an image, which is preferably an RGB video image, shown through surgical field display means for displaying the surgical field in a plan view. In an even more particular example, the central processing unit (5) calculates the distance between each point of the surface(S) of the tissue and the reference surface (RS) closest to each point and shows said distances to the user through the surgical field display means by superimposing the information on the RGB image. A specific way of showing information about the depth is the use of a color palette or a depiction by means of levels which distinguish regions at different depths.

Both types of input means can be arranged in an interface serving as an intermediate between the user and the central processing unit (5).

Figure 4:
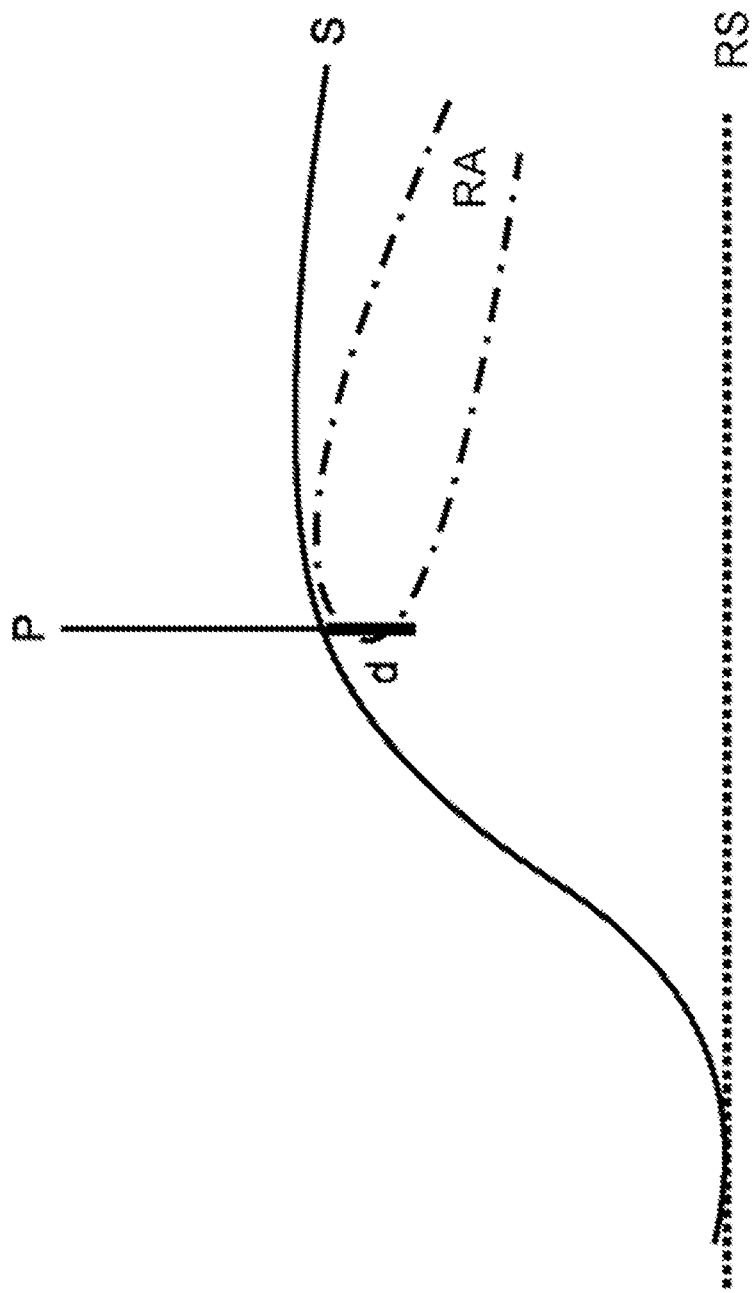
FIG. 4 shows a situation in which the central processing unit deactivates the laser for interacting with an area to be avoided.

FIG. 4 shows an example of a reference surface (RS) and a region to be avoided (RA) defined by the surgeon through input means, particularly an interface, of the central processing unit (5). The central processing unit (5) then assigns the surface and the shape of the region to be avoided (RA) to the numerical model (NM).

Additionally, this FIG. 4 shows a point P of the surface(S) on which the laser beam (1), for which the central processing unit (5) has ordered its deactivation, strikes. As can be seen, according to the numerical model (NM), a set of points of the segment defined between the intersection of the straight line, representing the laser beam, with the surface(S) of the tissue and said intersection plus a distance equal to the sectioning depth (d) are within the region to be avoided (RA). Therefore, given that sectioning is prohibited in the region to be avoided (RA), the laser must be deactivated at said point P.

In one example, the central processing unit (5) comprises other safety mechanisms to prevent the laser from being activated in risky situations.

On one hand, the central processing unit (5) comprises means for stopping the emission of the laser emitter (1) adapted for stopping the emission of the laser emitter (1) when it is operating. These means for stopping can be used at any time during the surgery when the medical personnel deem it appropriate.

Moreover, simultaneously or alternatively, the central processing unit (5) is further configured for deactivating the laser emitter (1) if, in the numerical model (NM), none of the positions of the points of the straight line, representing the laser beam, coincides with the position of a point of the surface(S) of the tissue. This measure seeks to prevent the laser from being activated when it is not well positioned over the surgical region (R) or when information about the actual surface(S) of the tissue is not available, for example due to a failure in the optical module (3), so as to prevent sectioning critical tissues and non-target tissues. It also constitutes a safety measure in the case that the patient has yet to be positioned on the operating table.

Figure 5:
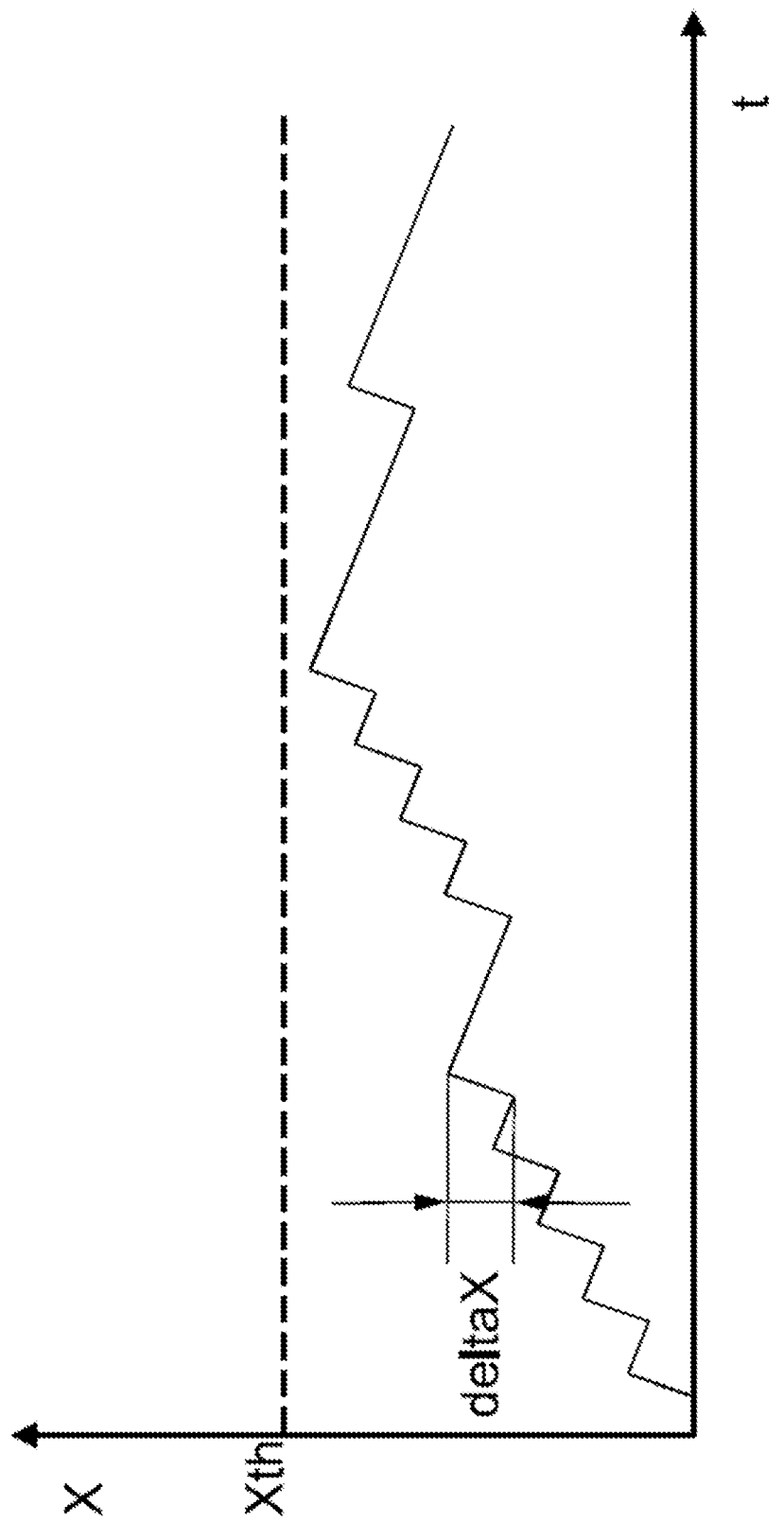
FIG. 5 shows an example of the temperature control of the tissues carried out by the device of the invention.

Lastly, FIG. 5 shows another safety measure of the device of the invention: laser power control per unit of surface to prevent the tissues from being thermally damaged.

To that end, the central processing unit (5) is further configured for defining a function representing a scalar (X) representative of the temperature level in a set of points of the region (R) with a specific pattern, wherein:
  the function initially takes a pre-established reference value, for example zero;

every time the laser emitter (1) strikes a point of the pattern, the function is increased at that point by a first pre-established incremental value (deltaX);

the values of all the points are reduced at every pre-established time period by a second pre-established incremental value;

for each point of the pattern, if it exceeds a pre-established threshold value (Xth), said point is assigned in the numerical model (NM) as the point where sectioning is not allowed as long as it remains above said threshold value (Xth).

The device thereby regulates the laser power per unit of surface so that it does not exceed the predefined threshold (Xth). This threshold (Xth) can be a dynamic threshold or can gradually change throughout the surgical intervention. In one example, the user, surgeon, or medical personnel selects the threshold (Xth) at a given time of the operation and enters same through input means of the central processing unit (5) which are preferably an interface. The pre-established time period can be a fixed or dynamic time period during the surgery. Furthermore, it can be selected at a given time of the surgery by the user or medical personnel who will enter the value in the central processing unit (5) through input means. In this example, the surgeon selects a fixed time period at the start of the operation.

In one example, the device described in any of the figures further comprises a fluid management unit, not shown in any of said figures, to provide the device with the capacity for cleaning the surgical region (R). This unit is adapted for providing, in the operating mode, a flow of a gas, of a liquid, or of a mist with liquid particles in gas, in a region containing the region (R) of biological tissue on which the laser emitter (1) acts.

The invention claimed is:

1. A biological tissue sectioning device, comprising:
    a laser emitter adapted for sectioning biological tissue in a region;
    a controller, in communication with the laser emitter, adapted for activating and deactivating the laser emitter;
    an optical module adapted for determining a surface of a tissue of the region in an operating mode; and
    a central processing unit, in communication with the controller and with the optical module, adapted for:
        defining at least one reference surface;
        generating a numerical model of the region comprising, at least:
            a shape of the surface of the tissue of the region,
            a shape of the at least one reference surface, under which sectioning is prohibited,
            a direction of a laser beam in which the laser emitter is oriented; and
        activating the laser emitter if, in the numerical model, at least one position corresponding to at least one point of a straight line, representing the laser beam, and spaced from an intersection of the same straight line with the surface of the tissue by a distance equal to a sectioning depth, is located outside a prohibited region, said prohibited region being any of parts of the tissue of the region in which sectioning is prohibited.

2. The device according to claim 1, wherein the central processing unit is further configured for deactivating the laser emitter if, in the numerical model, the at least one position corresponding to the at least one point of the straight line, representing the laser beam, located between the intersection of said straight line with the surface of the tissue and said intersection plus a distance equal to the sectioning depth, coincides with a position of at least one point of a prohibited region.

3. The device according to claim 1, wherein the central processing unit is further configured for deactivating the laser emitter if, in the numerical model, none of the at least one position corresponding to the point of the straight line, representing the laser beam, coincides with the position of a point of the surface of the tissue.

4. The device according to claim 1, wherein the at least one reference surface is:
    a boundary surface demarcating an end of the tissue of the region; or
    a boundary surface demarcating a start of a different tissue with respect to the tissue of the region the surface of which has been determined by the optical module, said different tissue being located at a greater depth than the tissue of the region; or
    a boundary surface demarcating the end of a different tissue with respect to the tissue of the region the surface of which has been determined by the optical module, said different tissue being located at a greater depth than the tissue of the region; or
    a combination of any of the foregoing.

5. The device according to claim 1, wherein the at least one reference surface is a flat surface essentially parallel to a focal plane of the laser emitter and/or to a focal plane of the optical module.

6. The device according to claim 1, wherein the at least one reference surface is a surface with a maximum depth determined from the surface of the tissue.

7. The device according to claim 1, wherein the at least one reference surface is:
    a flat surface essentially parallel to a focal plane of the laser emitter and/or to a focal plane of the optical module; and/or
    a surface with a maximum depth determined from the surface of the tissue; and/or
    a boundary surface demarcating an end of the tissue of the region; and/or
    a boundary surface demarcating a start of a different tissue with respect to the tissue of the region the surface of which has been determined by the optical module, said different tissue being located at a greater depth than the tissue of the region; and/or
    a boundary surface demarcating the end of a different tissue with respect to the tissue of the region the surface of which has been determined by the optical module, said different tissue being located at a greater depth than the tissue of the region.

8. The device according to claim 1, wherein the central processing unit defines the at least one reference surface with a safety margin.

9. The device according to claim 8, wherein the central processing unit comprises input means for inputting a definition of the safety margins of the at least one reference surface.

10. The device according to claim 1, wherein the optical module comprises an optical coherence tomography OCT system.

11. The device according to claim 10, wherein the optical coherence tomography system is a polarization-sensitive optical coherence tomography PS-OCT system.

12. The device according to any of claim 1, wherein the optical module comprises a system of:
- structured light type; or
- stereo pair type; or
- optoacoustic tomography type.

13. The device according to claim 1, wherein the laser emitter comprises a scanner which allows changing the direction of the laser beam so as to aim it at different points of the region.

14. The device according to claim 13, wherein the central processing unit is adapted for carrying out a continuous scanning of the laser beam emitted by the laser emitter over the region until reaching the at least one reference surface.

15. The device according to claim 14, wherein in the numerical model generated by the central processing unit, at least one flat surface is established progressively in a plurality of depth levels with respect to a focal plane of the laser emitter and/or the focal plane of the optical module, such that the at least one flat surface changes to a greater depth when the surface of the tissue has descended to the depth of said flat surface as a result of an action of the laser of the laser emitter.

16. The device according to claim 13, wherein the central processing unit is further configured so that, during a sectioning process while the laser emitter scans a set of points of the region, every time a sequence of points reaches a point where an emission of the laser emitter is hindered, the laser emitter is positioned in a next point at which the emission is allowed without stopping the emission of the laser beam.

17. The device according to claim 13, wherein the central processing unit is further configured so that, during a sectioning process while the laser emitter scans a set of points of the region, the points where the sectioning depth is smaller than others are given priority in a scanning sequence so as to compensate for the sectioning depth.

18. The device according to claim 1, wherein the optical module comprises an optical source and a scanner which allows changing the direction of the optical source so as to aim it at different points of the region.

19. The device according to claim 18, wherein the central processing unit is adapted for carrying out a continuous scanning of the optical source of the optical module over the region.

20. The device according to claim 18, wherein the control of the scanning established by the laser emitter and the scanning established by the optical module are independent.

21. The device according to claim 19, wherein the scanning of the optical source of the optical module over the region is performed when an obsolescence criterion selected from the following is met:
- after a pre-established time period has elapsed,
- prior to the activation or deactivation of the laser emitter by the central processing unit.

22. The device according to claim 1, wherein the central processing unit comprises input means for inputting a definition of the at least one reference surface which are assigned to the numerical model.

23. The device according to claim 22, wherein the at least one reference surface is determined by means of a preoperative image, preferably by means of a magnetic resonance image, computerized axial tomography image, or fluoroscopy image.

24. The device according to claim 23, wherein the at least one reference surface determined by means of a preoperative image is a boundary surface demarcating an end of a bone tissue of the region.

25. The device according to claim 1, wherein:
- the central processing unit comprises input means for inputting a definition of a region to be avoided, a shape of which is assigned to the numerical model; and
- the central processing unit is further configured for deactivating the laser emitter if, in the numerical model, at least one of the positions of the points of the straight line, representing the laser beam, located between the intersection of said straight line with the surface of the tissue and said intersection plus a distance equal to the sectioning depth, coincides with the position of at least one point of the region to be avoided.

26. The device according to claim 1, comprising surgical field display means, preferably a screen showing an RGB video image.

27. The device according to claim 26, wherein the surgical field display means further show information about the distance from each point of the surface of the tissue to the at least one reference surface.

28. The device according to claim 1, wherein the central processing unit is further configured for defining a function representing a scalar representative of a temperature level in a set of points of the region with a specific pattern, wherein:
- the function initially takes a pre-established reference value;
- every time the laser emitter strikes a point of the specific pattern, the function is increased at that point by a first pre-established incremental value (deltaX);
- values of all the points are reduced at every pre-established time period by a second pre-established incremental value; and
- for each point of the specific pattern, if it exceeds a pre-established threshold value (Xth), said point is assigned in the numerical model as the point where sectioning is not allowed as long as it remains above the pre-established threshold value (Xth).

29. The device according to claim 1, wherein the central processing unit comprises means for stopping an emission of the laser emitter adapted for stopping the emission of the laser emitter when it is operating.

30. The device according to claim 1, wherein the device further comprises a fluid management unit adapted for providing, in the operating mode, a flow of a gas, or of a liquid, or of a mist with liquid particles in gas, in a region containing the region of biological tissue on which the laser emitter acts.

* * * * *